(12) United States Patent
Chen et al.

(10) Patent No.: US 11,426,627 B2
(45) Date of Patent: Aug. 30, 2022

(54) METHOD AND APPARATUS FOR COUNTING FOOT STEP BASED ON ACCELERATION INFORMATION, AND DEVICE

(71) Applicant: Huawei Technologies Co., Ltd., Shenzhen (CN)

(72) Inventors: Yixin Chen, Shenzhen (CN); Chen Dong, Beijing (CN); Xiaohan Chen, Shenzhen (CN); Yu Wang, Beijing (CN)

(73) Assignee: HUAWEI TECHNOLOGIES CO., LTD., Shenzhen (CN)

(*) Notice: Subject to any disclaimer, the term of this patent is extended or adjusted under 35 U.S.C. 154(b) by 367 days.

(21) Appl. No.: 16/640,850

(22) PCT Filed: Aug. 23, 2017

(86) PCT No.: PCT/CN2017/098590
§ 371 (c)(1),
(2) Date: Feb. 21, 2020

(87) PCT Pub. No.: WO2019/036926
PCT Pub. Date: Feb. 28, 2019

(65) Prior Publication Data
US 2020/0398109 A1    Dec. 24, 2020

(51) Int. Cl.
*A63B 24/00* (2006.01)
*G06F 3/01* (2006.01)
(Continued)

(52) U.S. Cl.
CPC ........ *A63B 24/0006* (2013.01); *A61B 5/1118* (2013.01); *A63B 24/0062* (2013.01);
(Continued)

(58) Field of Classification Search
None
See application file for complete search history.

(56) References Cited

U.S. PATENT DOCUMENTS

2009/0043531 A1   2/2009  Kahn et al.
2009/0144020 A1   6/2009  Ohta et al.
(Continued)

FOREIGN PATENT DOCUMENTS

CN    103604441 A    2/2014
CN    104406604 A    3/2015
(Continued)

OTHER PUBLICATIONS

Zhong, S., et al., "An Accurate and Adaptive Pedometer Integrated in Mobile Health Application," IET International Conference on Wireless Sensor Network 2010 (IET-WSN 2010), Nov. 15-17, 2010, pp. 78-83.
(Continued)

*Primary Examiner* — Raul J Rios Russo
*Assistant Examiner* — Carl F. R. Tchatchouang
(74) *Attorney, Agent, or Firm* — Conley Rose, P.C.

(57) ABSTRACT

A method includes collecting an original signal in a specified time interval, performing combined acceleration processing on the original signal to obtain a combined acceleration signal, combining n data points of the combined acceleration signal into one data segment, extracting a feature point of the data segment, transforming feature points of all data segments into a feature point signal, analyzing the feature point signal to obtain a stable stage and a fluctuation stage of the feature point signal, performing interference period elimination on the feature point signal with the stable stage and the fluctuation stage according to a specified motion rule to obtain a second feature point signal, and counting a quantity of wave crests of the second feature point signal, where the quantity of wave crests is a quantity of steps.

20 Claims, 19 Drawing Sheets

(51) Int. Cl.
*A61B 5/11* (2006.01)
*G01C 22/00* (2006.01)

(52) U.S. Cl.
CPC ............ *G01C 22/006* (2013.01); *G06F 3/011* (2013.01); *G06F 3/017* (2013.01); *A61B 2562/0219* (2013.01); *A63B 2024/0012* (2013.01); *A63B 2220/17* (2013.01); *A63B 2220/40* (2013.01)

(56) References Cited

U.S. PATENT DOCUMENTS

| | | | |
|---|---|---|---|
| 2011/0054359 A1* | 3/2011 | Sazonov | A61B 5/1118 600/595 |
| 2015/0185044 A1 | 7/2015 | Nie et al. | |
| 2015/0293143 A1 | 10/2015 | Zao et al. | |

FOREIGN PATENT DOCUMENTS

| | | |
|---|---|---|
| CN | 104567912 A | 4/2015 |
| CN | 103997572 B | 1/2016 |
| CN | 105771187 A | 7/2016 |
| CN | 103712632 B | 8/2016 |
| CN | 205785240 U | 12/2016 |
| CN | 106289309 A | 1/2017 |
| WO | 2017001688 A1 | 1/2017 |

OTHER PUBLICATIONS

Li, H., "Study of Activities Classify and Step Detection Base on the Three-Dimensional Acceleration Sensor," Jun. 15, 2011, 46 pages.
Hu, Z., "The Research of Human Activity State Recognition Base on Accelerometers," Feb. 15, 2017, 57 pages.
Gowda, A., et al., "UMOISP: Usage Mode and Orientation Invariant Smartphone Pedometer," IEEE Sensors Journal, vol. 17, No. 3, Feb. 1, 2017, 13 pages.

* cited by examiner

METHOD AND APPARATUS FOR COUNTING FOOT STEP BASED ON ACCELERATION INFORMATION, AND DEVICE

CROSS-REFERENCE TO RELATED APPLICATIONS

This application is a U.S. National Stage of International Patent Application No. PCT/CN2017/098590 filed Aug. 23, 2017, which is hereby incorporated by reference in its entirety.

TECHNICAL FIELD

This application relates to the communications field, and in particular, to a method and an apparatus for counting a foot step based on acceleration information, and a device.

BACKGROUND

Under guidance of the national fitness program, running exercise is popular among people, and there is a huge market opportunity for wearable sports devices. A fitness record is a basic exercise and fitness function of the wearable sports device, and is mainly used to implement step counting, distance recording, exercise time recording, energy consumption calculation, and the like. Most users have a requirement for this function. The step counting is a most intuitive exercise indicator in the fitness record, so that the users can directly assess their respective exercise amounts. In addition, step counting is combined with a related social APP, and becomes an important part of exercise socialization.

Step counting is implemented when an existing wearable sports device is worn on the wrist and around the waist. For example, if a user wears the wearable sports device on the foot, step counting cannot be implemented. Therefore, an existing technical solution cannot implement foot step counting.

SUMMARY

A technical problem to be resolved in embodiments of this application is to provide a method for counting a foot step based on acceleration information, to resolve a prior-art problem that foot step counting cannot be implemented.

According to a first aspect, a method for counting a foot step based on acceleration information is provided. The method includes the following steps: collecting an original signal in a specified time interval, and performing combined acceleration processing on the original signal to obtain a combined acceleration signal; combining n data points of the combined acceleration signal into one data segment, extracting a feature point of the data segment, and transforming feature points of all data segments into a feature point signal, where the feature point is a sum of maximum fluctuation values of a front half segment and a rear half segment of each axis of the data segment; analyzing the feature point signal to obtain a stable stage and a fluctuation stage of the feature point signal, and performing interference period elimination on the feature point signal with the stable stage and the fluctuation stage according to a specified motion rule to obtain a feature point signal obtained after the interference elimination; and counting a quantity of wave crests of the feature point signal obtained after the interference elimination, where the quantity of wave crests is a quantity of steps.

The method for counting a foot step provided in the first aspect can implement foot step counting by processing the original signal.

In an optional solution, a value range of n is an integer within [8, 12].

In another optional solution, the analyzing the feature point signal to obtain a stable stage and a fluctuation stage of the feature point signal includes: when the feature point signal is considered as a stable stage of walking by default, extracting every m1 feature points of the feature point signal, determining a group of first amplitude differences between the m1 feature points and a group of first amplitude absolute-values of the m1 feature points, and if the group of first amplitude differences falls within a first specified range and the group of first amplitude absolute values is less than a first threshold, determining the m1 feature points as the stable stage of walking; if a group of second amplitude differences between m2 feature points after the m1 feature points falls within a second specified range and a group of second amplitude absolute-values of the m2 feature points is greater than the first threshold and less than a second threshold, determining the m2 feature points as a fluctuation stage of walking; searching a remaining interval of a feature point signal in a non-walking state for a stable stage of running, extracting every m3 feature points in the remaining interval, determining a group of third amplitude differences between the m3 feature points and a group of third amplitude absolute-values of the m3 feature points, and if the group of amplitude absolute-values of the m3 feature points is less than a third threshold and the group of third amplitude differences falls within the first specified range, determining the m3 feature points as the stable stage of running; and extracting the last m4 feature points after the m3 feature points, determining a group of fourth amplitude differences between the m4 feature points and a group of fourth amplitude absolute-values of the m4 feature points, and if the group of fourth amplitude absolute-values is greater than the third threshold and the group of fourth amplitude differences falls within the second specified range, determining the m4 feature points as a fluctuation stage of running, where values of m1, m2, m3, and m4 are all integers greater than or equal to 3.

In still another optional solution, the performing interference period elimination on the feature point signal with the stable stage and the fluctuation stage according to a specified motion rule to obtain a feature point signal obtained after the interference elimination includes: determining wave crest locations in the stable stage and the fluctuation stage, preliminarily determining each wave crest as a step quantity location, calculating a difference between two adjacent step quantities, sequentially forming all differences into a difference list, dividing the difference list into a walking state and a running state based on a corresponding step quantity location, searching the difference list in the walking state for an $x^{th}$ difference and an $(x+1)^{th}$ difference that are less than a first difference threshold, and if a sum of the $x^{th}$ difference and the $(x+1)^{th}$ difference is less than a second difference threshold, removing an intermediate wave crest of the $x^{th}$ difference and the $(x+1)^{th}$ difference; and searching the difference list in the running state for a $y^{th}$ difference and a $(y+1)^{th}$ difference that are less than a third difference threshold, and if a sum of the $y^{th}$ difference and the $(y+1)^{th}$ difference is less than a fourth difference threshold, removing an intermediate wave crest of the $y^{th}$ difference and the $(y+1)^{th}$ difference.

According to a second aspect, an apparatus for counting a foot step based on acceleration information is provided. The apparatus includes: a collection unit, configured to collect an original signal in a specified time interval; and a processing unit, configured to: perform combined acceleration processing on the original signal to obtain a combined acceleration signal; combine n data points of the combined acceleration signal into one data segment, extract a feature point of the data segment, and transform feature points of all data segments into a feature point signal, where the feature point is a sum of maximum fluctuation values of a front half segment and a rear half segment of each axis of the data segment; analyze the feature point signal to obtain a stable stage and a fluctuation stage of the feature point signal, and perform interference period elimination on the feature point signal with the stable stage and the fluctuation stage according to a specified motion rule to obtain a feature point signal obtained after the interference elimination; and count a quantity of wave crests of the feature point signal obtained after the interference elimination, where the quantity of wave crests is a quantity of steps.

According to a third aspect, a portable device is provided. The device includes a sensor, a processor, a memory, and a transceiver. The processor is connected to the sensor, the memory, and the transceiver. The sensor is configured to collect an original signal in a specified time interval. The processor is configured to: perform combined acceleration processing on the original signal to obtain a combined acceleration signal; combine n data points of the combined acceleration signal into one data segment, extract a feature point of the data segment, and transform feature points of all data segments into a feature point signal, where the feature point is a sum of maximum fluctuation values of a front half segment and a rear half segment of each axis of the data segment; analyze the feature point signal to obtain a stable stage and a fluctuation stage of the feature point signal, and perform interference period elimination on the feature point signal with the stable stage and the fluctuation stage according to a specified motion rule to obtain a feature point signal obtained after the interference elimination; and count a quantity of wave crests of the feature point signal obtained after the interference elimination, where the quantity of wave crests is a quantity of steps.

According to a fourth aspect, a computer-readable storage medium is provided. The computer-readable storage medium stores a computer program used to exchange electronic data, and the computer program enables a computer to perform the method in the first aspect.

According to a fifth aspect, a computer program product is provided. The computer program product includes a non-transitory computer-readable storage medium storing a computer program, and the computer program can be operated to enable a computer to perform the method according to the first aspect.

BRIEF DESCRIPTION OF DRAWINGS

To describe the technical solutions in the embodiments of this application or in the prior art more clearly, the following briefly describes the accompanying drawings required for describing the embodiments. Apparently, the accompanying drawings in the following description show merely some embodiments of this application, and a person of ordinary skill in the art may still derive other drawings from these accompanying drawings without creative efforts.

DESCRIPTION OF EMBODIMENTS

The following clearly and completely describes the technical solutions in the embodiments of this application with reference to the accompanying drawings in the embodiments of this application. Apparently, the described embodiments are merely some but not all of the embodiments of this application. All other embodiments obtained by a person of ordinary skill in the art based on the embodiments of this application without creative efforts shall fall within the protection scope of this application.

Figure 1A:
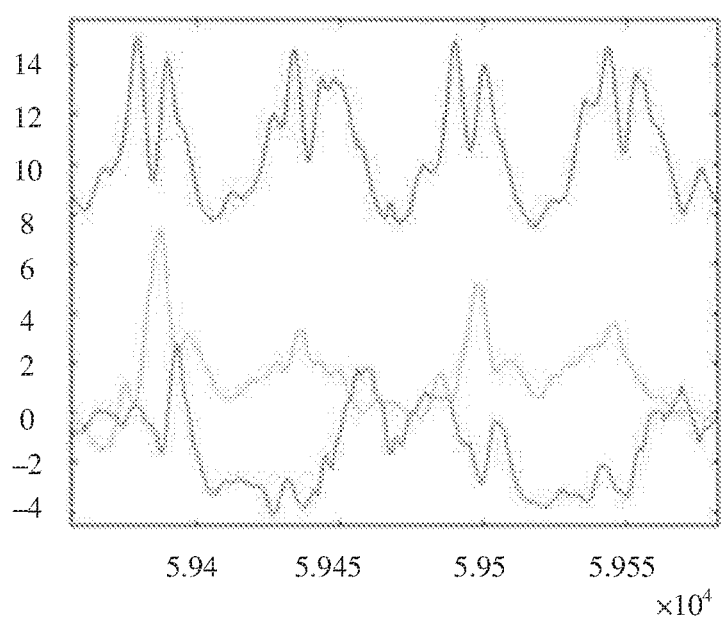
FIG. 1a is a waveform diagram of a hand walking signal.
Figure 1B:
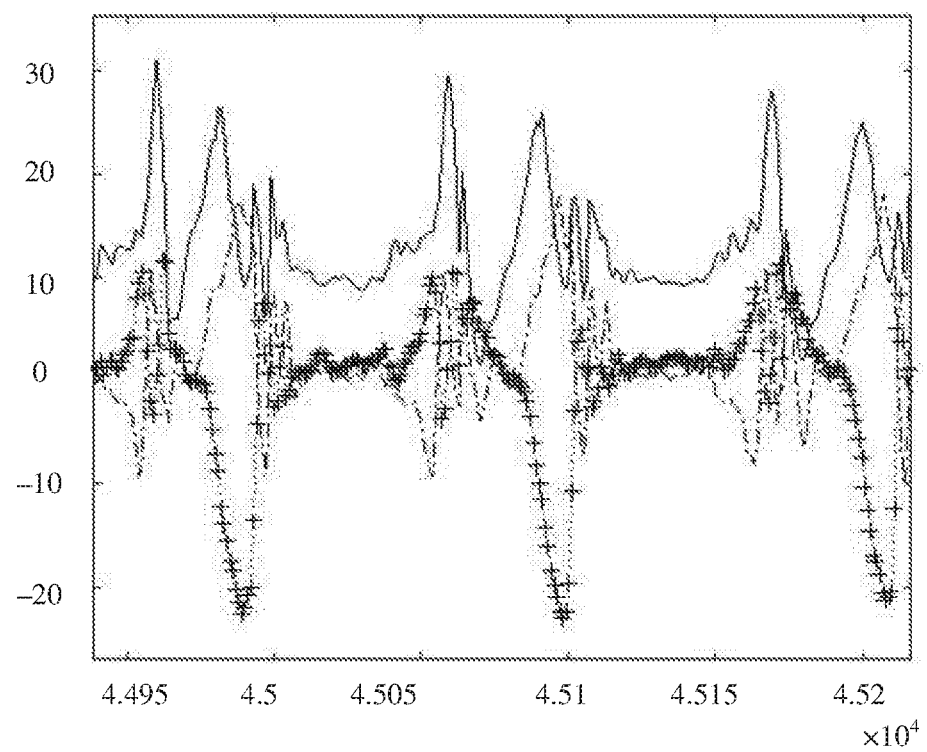
FIG. 1b is a waveform diagram of an ankle walking signal.

FIG. 1a is a waveform diagram of a hand walking signal in a specified time range. FIG. 1b is a waveform diagram of an ankle walking signal in a specified time range. Referring to FIG. 1a, the hand walking signal includes four periods, and acceleration amplitude of three axes is relatively small. A major wave crest (including some oscillation) can be seen in each period on an axis perpendicular to the ground, and amplitude keeps changing. Referring to FIG. 1b, a walking signal includes two periods, and acceleration amplitude of three axes is relatively large. An axis perpendicular to a ground has two wave crests in each period, and amplitude does not obviously change in a period. Due to these differences, a hand step counting method is inapplicable to foot step counting.

Figure 2:
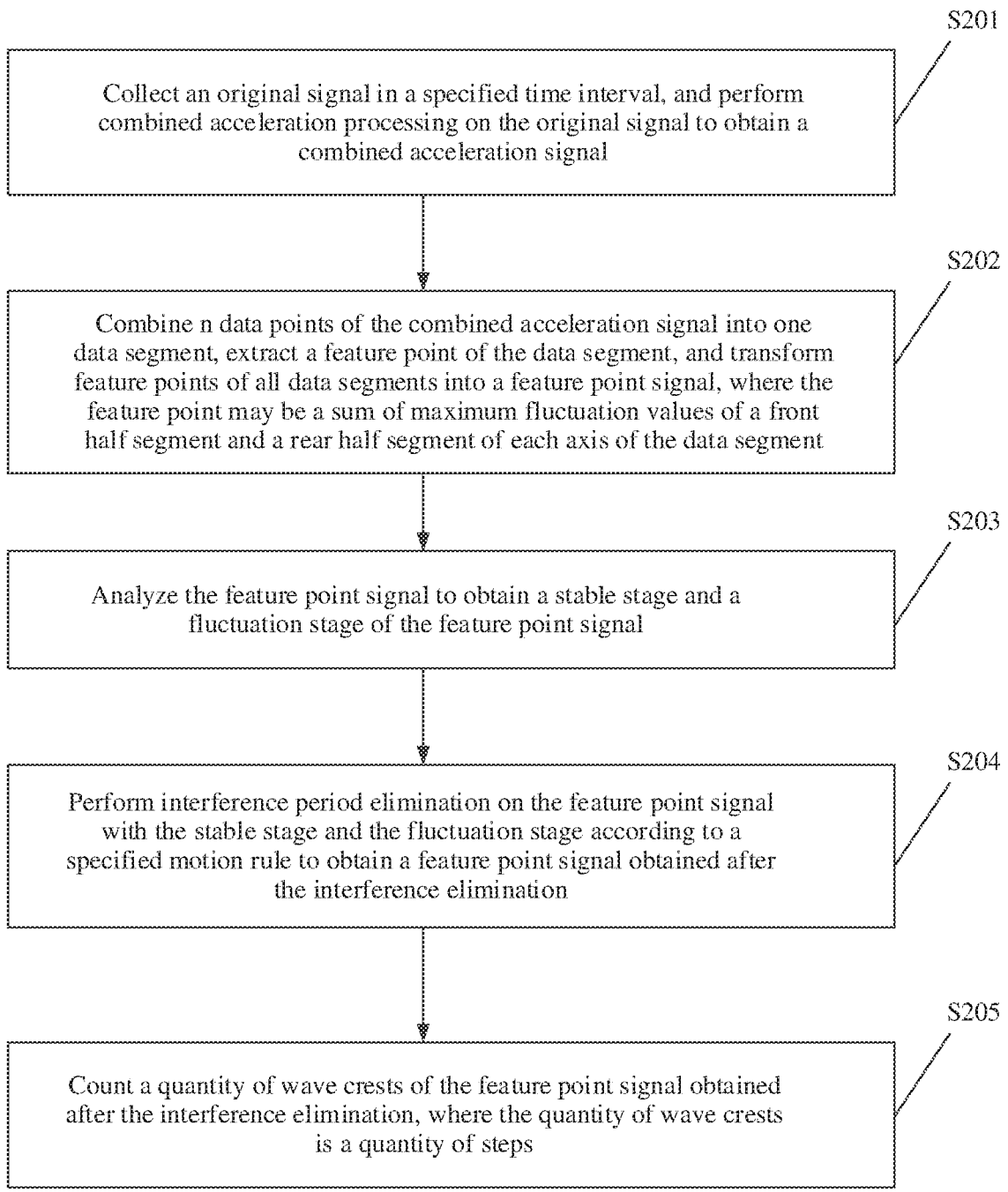
FIG. 2 is a schematic flowchart of a method for counting a foot step based on acceleration information according to an embodiment of this application.

FIG. 2 provides a method for counting a foot step based on acceleration information. The method is performed by a wearable device. As shown in FIG. 2, the method includes the following steps.

Step S201. Collect an original signal in a specified time interval, and perform combined acceleration processing on the original signal to obtain a combined acceleration signal.

Figure 2A:
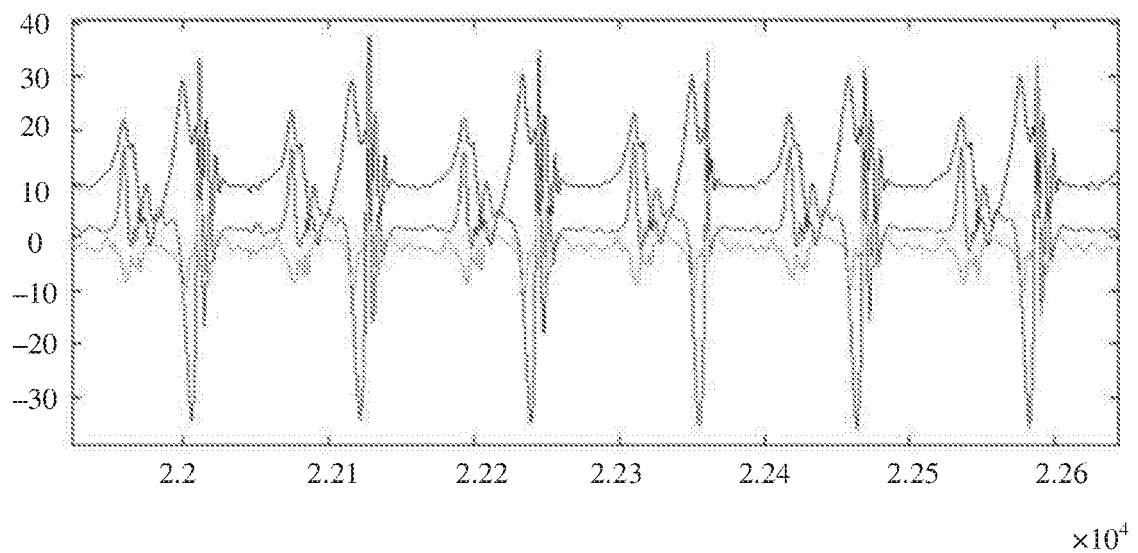
FIG. 2a is an original signal of an ankle collected in a specified time interval according to an embodiment of this application.
Figure 2B:
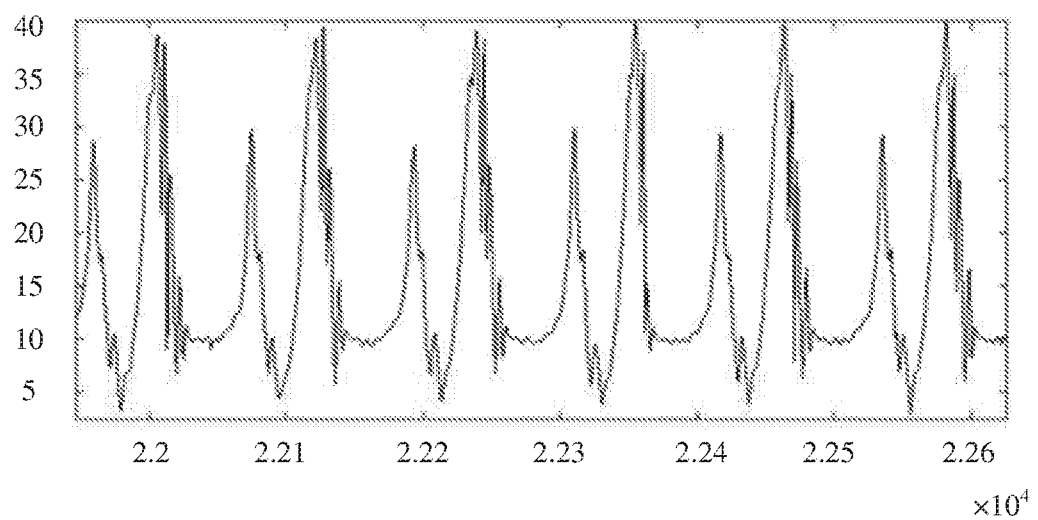
FIG. 2b is a schematic diagram of a combined acceleration signal according to an embodiment of this application.

As shown in FIG. 2a, the original signal in the specified time interval is collected. For example, the specified time interval is 5 s, and as shown in FIG. 2b, the combined acceleration processing is performed on the original signal to obtain the combined acceleration signal. The original signal shown in FIG. 2a may be a three-axis acceleration signal.

Step S202. Combine n data points of the combined acceleration signal into one data segment, extract a feature point of the data segment, and transform feature points of all data segments into a feature point signal. The feature point may be a sum of maximum fluctuation values of a front half segment and a rear half segment of each axis of the data segment. A method for calculating the maximum fluctuation values of the front half segment and the rear half segment may be as follows: Herein, each of the n data points is divided into a front segment and a rear segment (n is an even number, and for example, when n is an odd number, a value that is the same as the last data point may be supplemented at the end), and subtraction is separately performed on three-axis signal points of two segments on each axis (that is, $[y(6)-y(1), y(7)-y(2), \ldots,$ and $y(10)-y(5)]$), where $y(6), \ldots,$ and $y(10)$ may be values of a second segment, and $y(1), \ldots,$ and $y(5)$ may be values of a first segment; and n/2 differences on each axis are obtained, absolute values of the n/2 differences are calculated, and three maximum absolute values are obtained. A maximum fluctuation value is obtained by adding the three maximum absolute values.

Figure 2C:
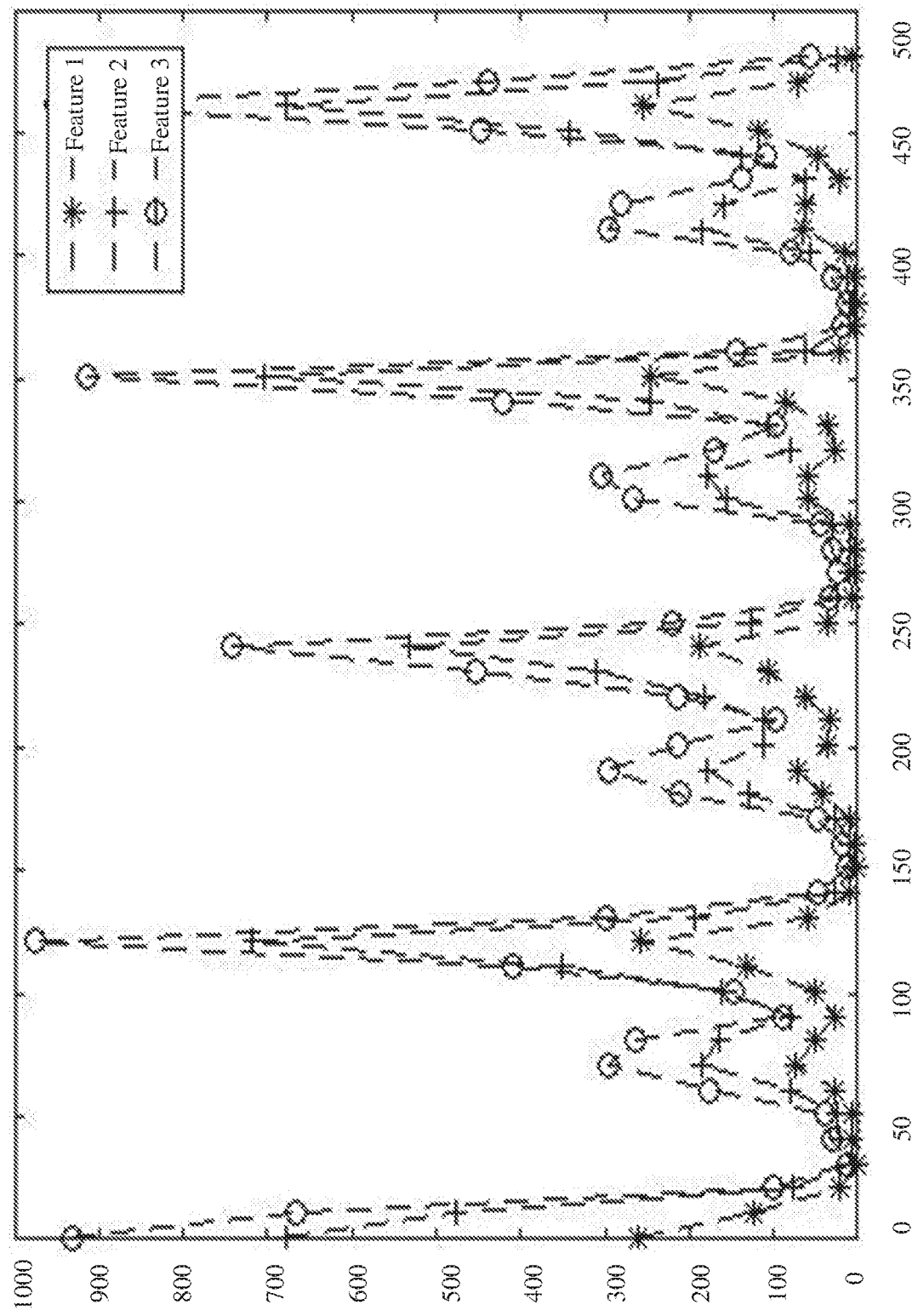
FIG. 2c is a schematic diagram of a feature point signal according to an embodiment of this application.

The foregoing n data points may be specifically integers within [8, 12]. Certainly, in actual application, another range may be further collected. FIG. 2c is a schematic diagram of a feature point signal when n is equal to 10. Certainly, the foregoing feature point may also be a maximum value of standard deviations of the data segment on each axis or a maximum value of differences between a maximum value and a minimum value the data segment on each axis.

Step S203. Analyze the feature point signal to obtain a stable stage and a fluctuation stage of the feature point signal.

Parameter ranges in the stable stage and the fluctuation stage are shown in Table 1.

TABLE 1

| Feature point difference | Walking | Running |
| --- | --- | --- |
| Stable stage | With a stable amplitude that is below 10 | With a stable feature amplitude that is between 10 and 40 |
| Fluctuation stage | Peak value is lower | Peak value is higher |

A method for implementing step S203 may be specifically as follows:

The feature point signal is considered as a stable stage of walking by default. Every m1 feature points of the feature point signal are extracted. A group of first amplitude differences between the m1 feature points and a group of first amplitude absolute-values of the m1 feature points are determined. If the group of first amplitude differences falls within a first specified range and the group of first amplitude absolute-values is less than a first threshold, the m1 feature points are determined as the stable stage of walking. If a group of second amplitude differences between m2 feature points after the m1 feature points falls within a second specified range and a group of second amplitude absolute-values of the m2 feature points is greater than the first threshold and less than a second threshold, the m2 feature points are determined as a fluctuation stage of walking. A remaining interval of a feature point signal in a non-walking state is searched for a stable stage of running. Every m3 feature points in the remaining interval are extracted. A group of third amplitude differences between the m3 feature points and a group of third amplitude absolute-values of the m3 feature points are determined. If the group of amplitude absolute-values of the m3 feature points is less than a third threshold and the group of third amplitude differences falls within the first specified range, the m3 feature points are determined as the stable stage of running. The last m4 feature points after the m3 feature points are extracted. A group of fourth amplitude differences between the m4 feature points and a group of fourth amplitude absolute-values of the m4 feature points are determined. If the group of fourth amplitude absolute-values is greater than the third threshold and the group of fourth amplitude differences falls within the second specified range, the m4 feature points are determined as a fluctuation stage of running. Values of m1, m2, m3, and m4 are all integers greater than or equal to 3.

The third threshold is greater than the first threshold, and the fourth threshold is greater than the second threshold.

Figure 2D:
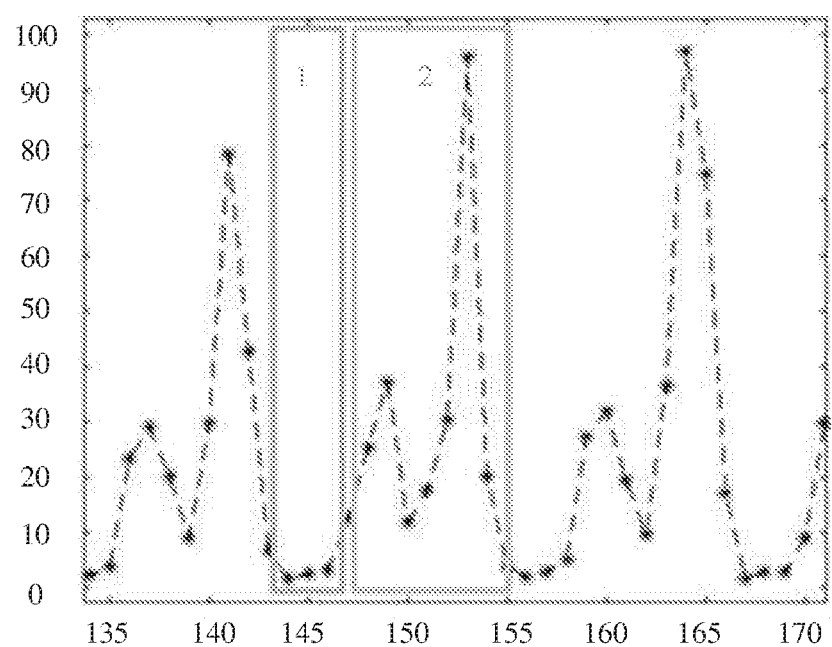
FIG. 2d is a schematic diagram of two stages of a walking state.
Figure 2E:
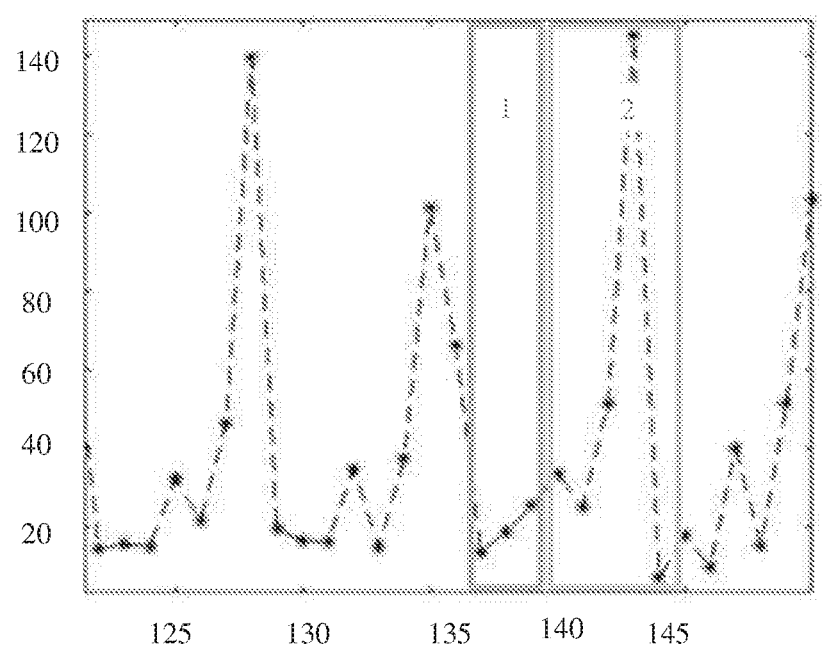
FIG. 2e is a schematic diagram of two stages of a running state.

FIG. 2d is a schematic diagram of a stable stage of walking and a fluctuation stage of walking. FIG. 2e is a schematic diagram of a stable stage of running and a fluctuation stage of running. An interval 1 indicates a stable stage, and an interval 2 indicates a fluctuation stage.

Different specific steps are identified based on a determined motion state by using different constraint conditions. The constraint conditions are as follows:

Condition A: By observing a foot signal, impact caused by foot grounding is short and strong. Therefore, a maximum feature value in the fluctuation stage needs to be in a forefront column in an order of amplitude values in an entire period. The forefront column may specifically include the first p amplitudes, and p may be an integer less than or equal to 7.

Condition B: A feature amplitude of impact is relatively large, and a minimum feature threshold is required.

Condition C: For a foot walking signal, a fluctuation in a stable stage is very slight. Therefore, a ratio of a standard deviation of a feature in the fluctuation stage to a standard deviation of that in the stable stage is relatively large.

Condition D: For a foot running signal, signal energy is relatively large, and a minimum energy threshold in the fluctuation stage is required (combined acceleration needs to be greater than the minimum threshold).

For amplitudes of the walking state (which may be specifically divided into a stable stage of walking and a fluctuation stage of walking) and the running state (which may be specifically divided into a stable stage of running and a fluctuation stage of running), the amplitude of the fluctuation stage of walking is usually greater than the amplitude of the stable stage of running (in other words, the second threshold may be greater than the third threshold). A relationship between amplitudes is: walking stableness<running stableness<walking fluctuation<running fluctuation, in other words, first threshold<third threshold<second threshold<fourth threshold. For state determining, first, walking is considered by default. An absolute value of an amplitude of walking has a first threshold, and duration less than the first threshold needs to be between 0.2 s and 0.5 s (the stable stage). When the duration less than the first threshold is between 0.2 s and 0.5 s, a subsequent point greater than the first threshold needs to be found, and duration greater than the first threshold and less than the second threshold needs to be between 0.3 s and 1.5 s (the fluctuation stage). After the two conditions are met, it is determined whether the condition A, the condition B, and the condition C are met. If it is found that the condition A, the condition B, and the condition C are not met, it is determined whether the state is running, in other words, the third threshold needs to be set. It is determined that the stable stage of running (less than the third threshold) is between the 0.2 s and 0.5 s, the fluctuation stage (greater than the third threshold and less than the fourth threshold) is between 0.3 s to 1 s, and the condition A, the condition B, and the condition D needs to be met, to determine that the state is a running state.

A threshold used in each condition is an adaptive threshold, and is related to parameters such as a state flag of a previous window, a peak point location of each period, a corresponding feature value, and a time flag. In other words, the threshold may be adjusted based on a corresponding threshold of the previous window. A specific adjustment manner is as follows: The threshold may be dynamically adjusted through weighted averaging or direct averaging.

Step S204: Perform interference period elimination on the feature point signal with the stable stage and the fluctuation stage according to a specified motion rule to obtain a feature point signal obtained after the interference elimination.

A method for implementing step S204 may be specifically as follows:

Wave crest locations in the stable stage and the fluctuation stage are determined. Each wave crest is preliminarily determined as a step quantity location. A difference between two adjacent step quantities is calculated. All differences are sequentially formed into a difference list. The difference list is divided into a walking state (a sum of the stable stage of walking and the fluctuation stage of walking) and a running state (a sum of the stable stage of running and the fluctuation stage of running) based on a corresponding step quantity location. The difference list in the walking state is searched for an $x^{th}$ difference and an $(x+1)^{th}$ difference that are less than a first difference threshold. If a sum of the $x^{th}$ difference and the $(x+1)^{th}$ difference is less than a second difference threshold (greater than the first difference threshold), an intermediate wave crest of the $x^{th}$ difference and the $(x+1)^{th}$ difference is removed. The difference list in the running state is searched for a $y^{th}$ difference and a $(y+1)^{th}$ difference that are less than a third difference threshold, and if a sum of the $y^{th}$ difference and the $(y+1)^{th}$ difference is less than a fourth difference threshold (greater than the third difference threshold), an intermediate wave crest of the $y^{th}$ difference and the $(y+1)^{th}$ difference is removed.

The intermediate wave crest is described by using an actual example. It is assumed that there are three wave crests, which are respectively a wave crest 1, a wave crest 2, and a wave crest 3. In this case, $x^{th}$ difference=wave crest 2−wave crest 1, and $(x+1)^{th}$ difference=wave crest 3−wave crest 2. Therefore, the wave crest 2 is determined as the intermediate wave crest.

Step S205: Count a quantity of wave crests of the feature point signal obtained after the interference elimination, and the quantity of wave crests is a quantity of steps.

Optionally, the method may further include: updating parameters such as a state flag of a current window (namely, a specified time interval), a location of a peak point in each period, a corresponding feature value, and a time flag.

According to the technical solution provided in this application, step counting is performed on the quantity of steps based on the quantity of wave crests.

Figure 3A:
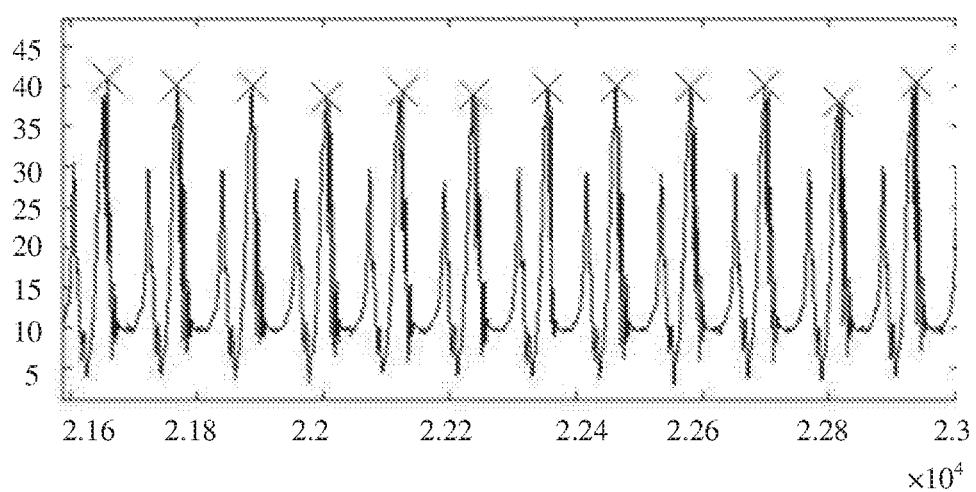
FIG. 3a is a schematic diagram of foot step counting according to this application.

When the technical solution of this application is applied, a step counting result is shown in FIG. 3a based on a three-axis acceleration sensor signal that is collected in advance.

As shown in FIG. 3a, an impact of foot grounded is regarded as a step. A tester walks 12 steps, and a step counting result is 12 steps.

Figure 3B:
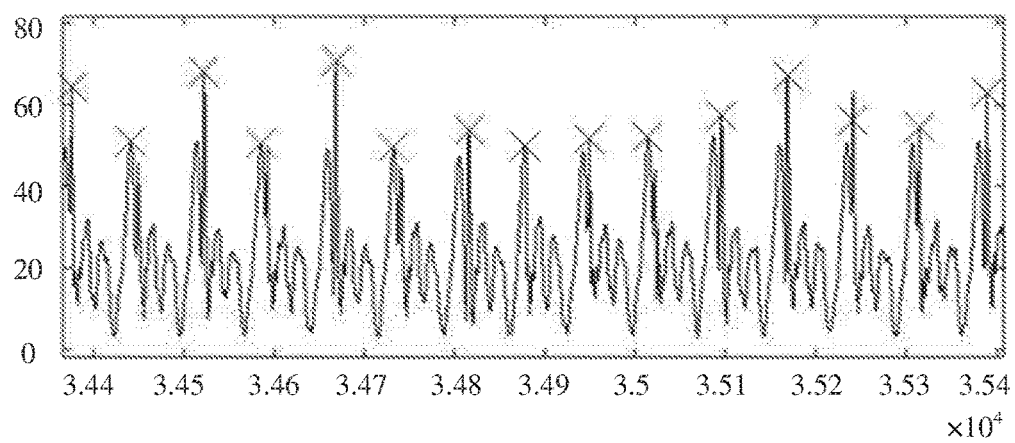
FIG. 3b is another schematic diagram of foot step counting according to this application.

As shown in FIG. 3b, an impact of foot grounded is regarded as a step. The tester walks 15 steps, and the step counting result is 15 steps.

After preliminary verification, step counting accuracy of a walking/running signal in this application is approximately 94%. An accuracy calculation manner is: accuracy=1−abs (quantity of steps calculated by step counting method−real quantity of steps)/real quantity of steps, abs represents that an absolute value is obtained.

Figure 3C:
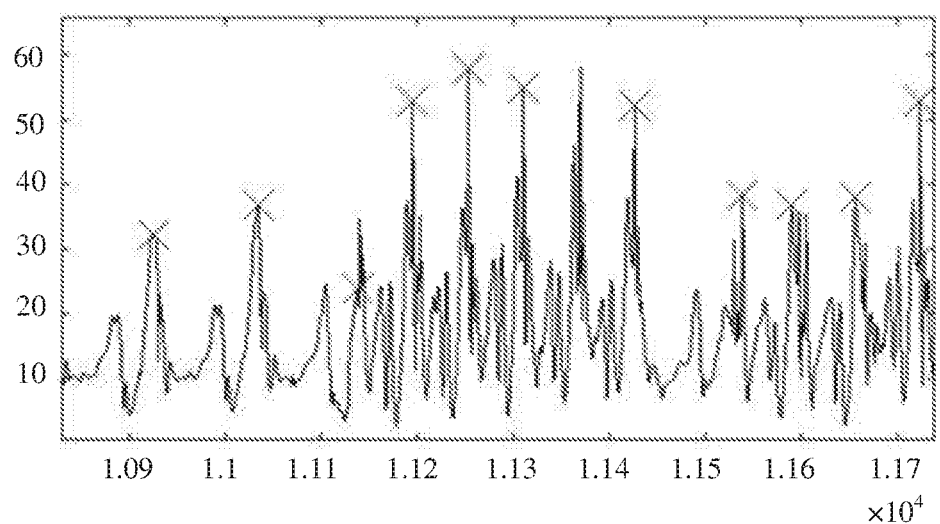
FIG. 3c is still another schematic diagram of foot step counting according to this application.

As shown in FIG. 3c, the tester goes downstairs 12 steps, and the step counting result is 11 steps.

Figure 3D:
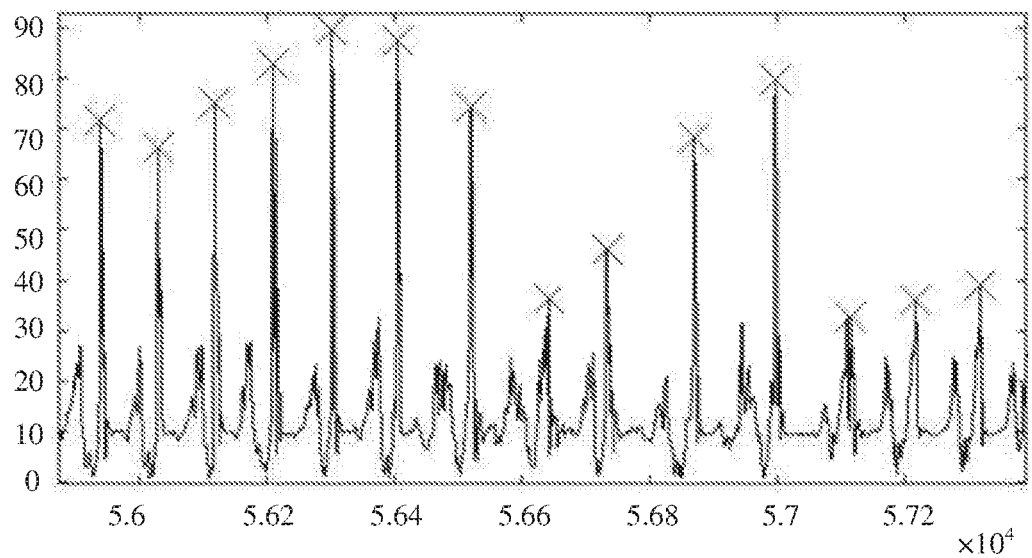
FIG. 3d is yet another schematic diagram of foot step counting according to this application.

As shown in FIG. 3d, the tester goes upstairs 14 steps, and the step counting result is 14 steps.

After preliminary verification, a particular processing capability is provided in this application for step counting of going upstairs or going downstairs.

Figure 4:
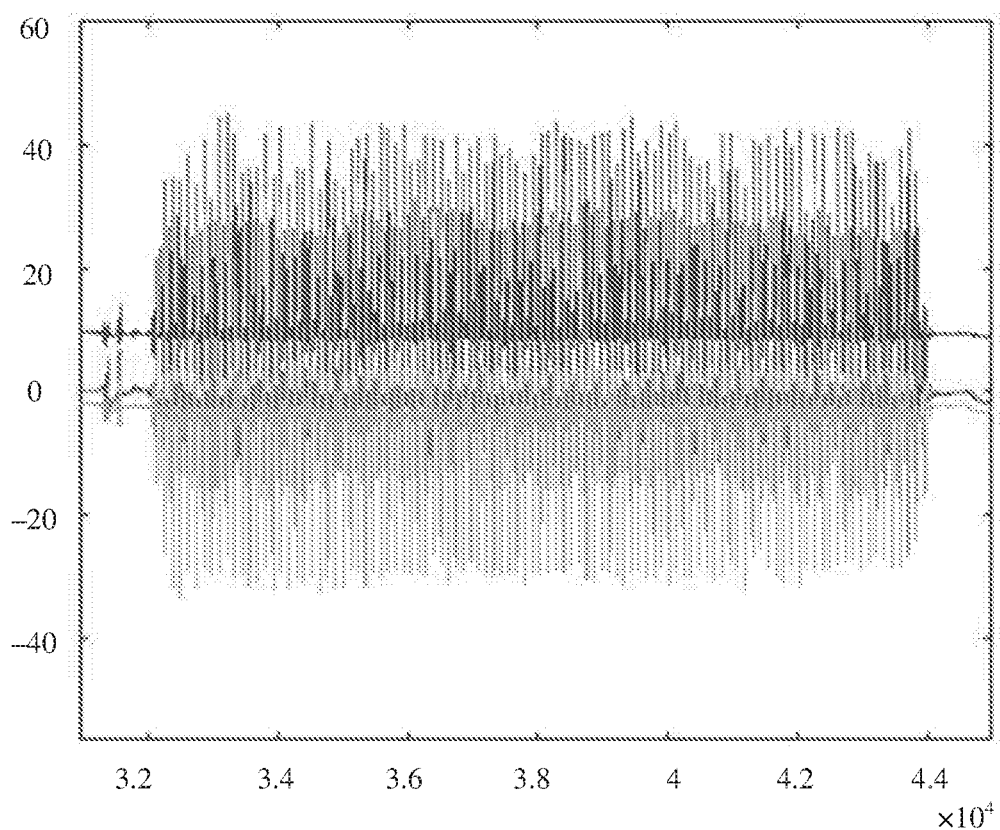
FIG. 4 is a schematic diagram of an input original signal.
Figure 4A:
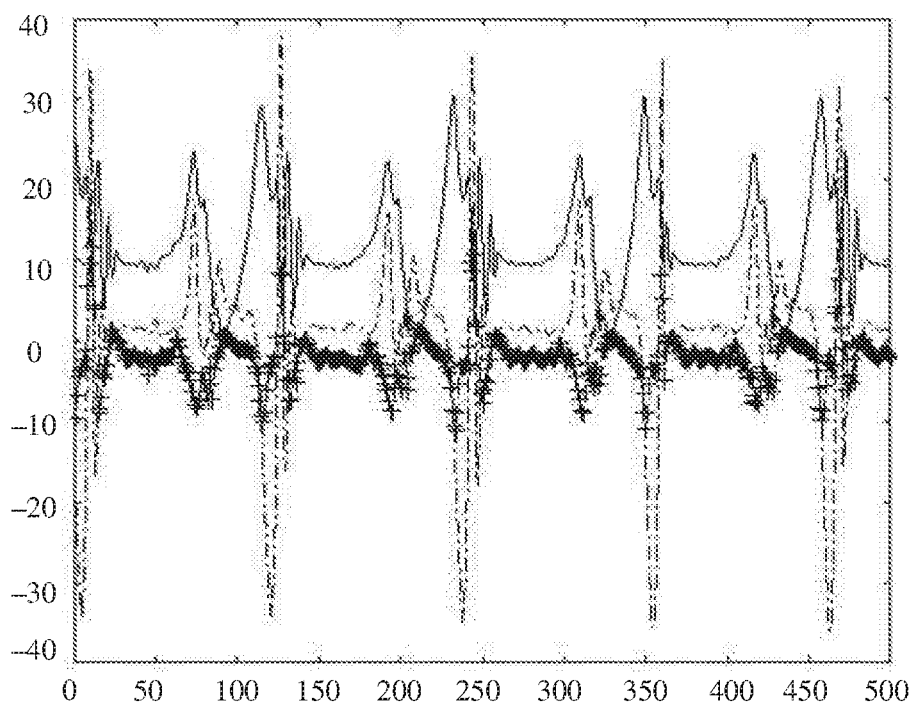
FIG. 4a is a schematic diagram of an original signal according to another embodiment of this application.

In another embodiment of this application, how to perform step counting in this application is described by using a foot signal of a tester as an example. As shown in FIG. 4, the tester walks 100 steps (one step of a wearing foot is counted as one step). As shown in FIG. 4a, a 10 s window signal is input.

Historical Parameter Reading

Parameters such as a state flag, a location of a peak point in each period, a corresponding feature value, and a time flag of a previous window are read-in.

Feature Extraction

Figure 4B:
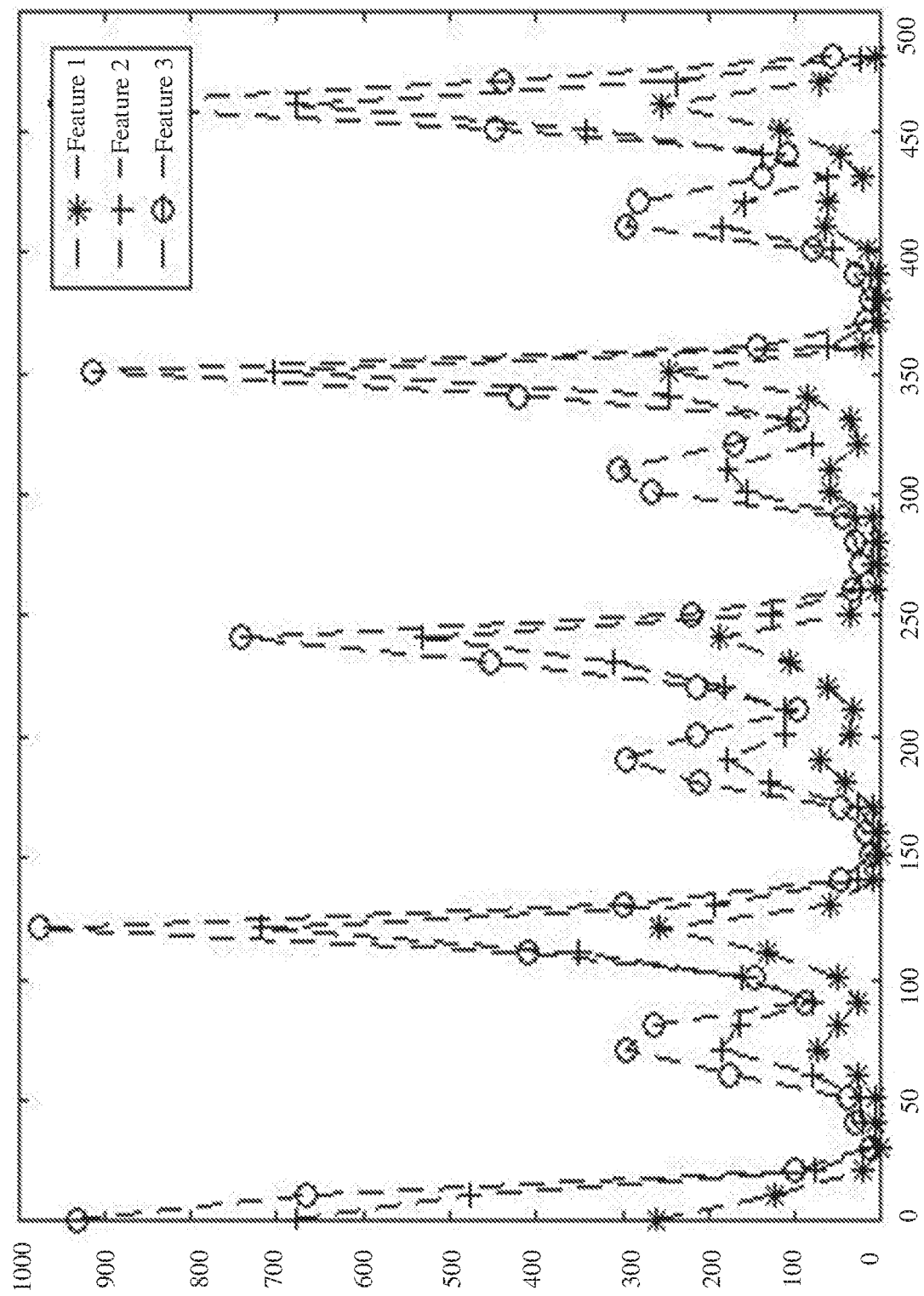
FIG. 4b is a schematic diagram of capturing a 10 s window from an original signal according to another embodiment of this application.

For a purpose of measuring a signal fluctuation amplitude and corresponding time, three features are extracted by using 10 data points as one data segment. The extracted features are shown in FIG. 4b.

Walking/Running Determining

Figure 4C:
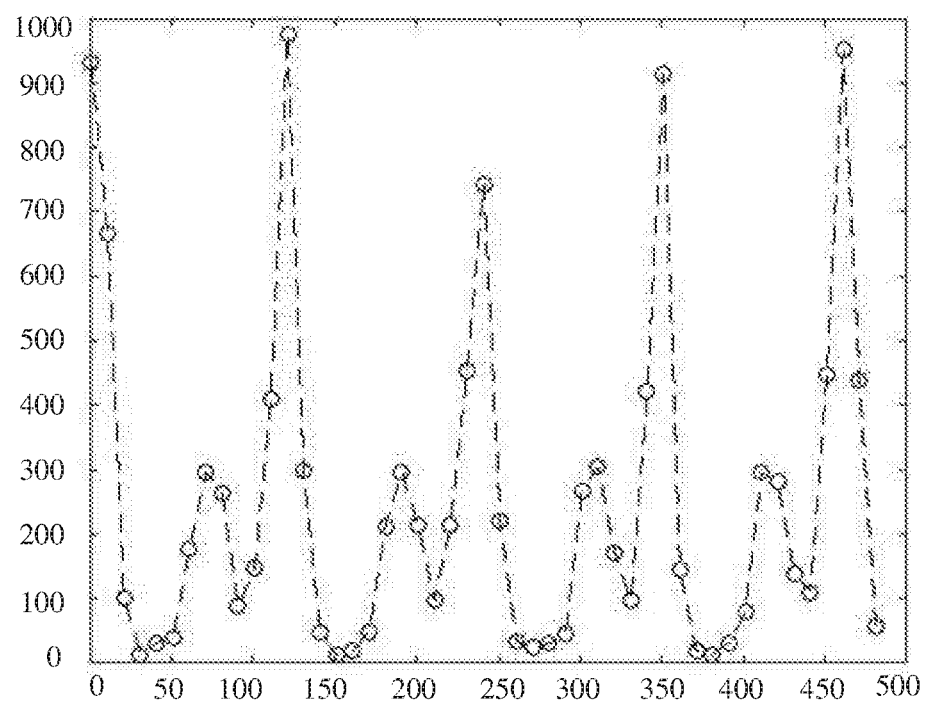
FIG. 4c is a schematic diagram of a feature point signal according to another embodiment of this application.
Figure 4D:
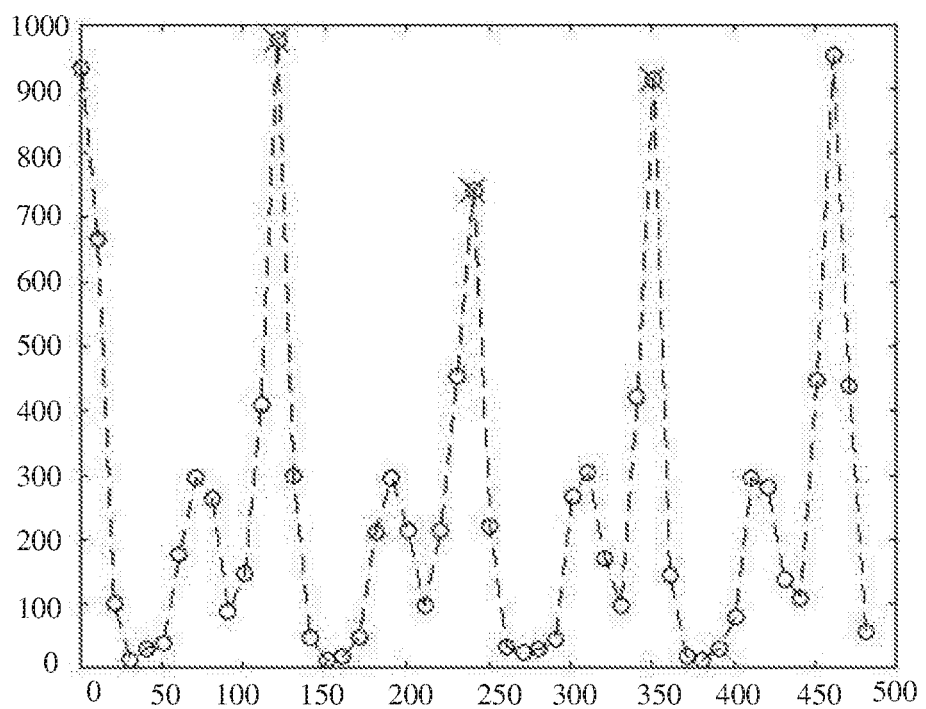
FIG. 4d is a schematic diagram of another feature point signal according to another embodiment of this application.

Start and end time points of a stable stage and a fluctuation stage are identified by using a difference that is between a walking signal and a running signal in the two stages. A feature 3 corresponding to a signal in the window is shown in FIG. 4c.

It may be determined, based on a feature difference, that the signal in the window is walking.

Initial Period Determining

Based on a determined motion state, different constraint conditions are used to identify each specific step. Constraint conditions are as follows:

By observing a foot signal, impact caused by foot grounding is short and strong. Therefore, a maximum feature value in the fluctuation stage needs to be in a forefront column in an order of amplitude values in an entire period (condition A).

An amplitude of an impact feature is relatively large, and a minimum threshold of the feature is required (condition B).

For a foot walking signal, a fluctuation in a stable stage is very small. Therefore, a ratio of a standard deviation of a feature in the fluctuation stage to a standard deviation in the stable stage is relatively large (condition C).

For a foot running signal, signal energy is relatively large, and a minimum threshold of energy in a fluctuation stage is required (condition D).

The found initial period is shown in FIG. 4c.

A cross represents a step. In this window, a tester walks 8 steps, and a step counting result is 6 steps. Here is a brief explanation of last two steps without a flag. In the last two steps, no feature sequence meeting a condition is found in the window, which is marked as an unprocessed signal, and continues to be processed in a next window.

Interference Period Elimination

A period determining mistakenly is eliminated according to a basic motion rule (walking time of each step is between 0.5 s and 2 s, and running time of each step is between 0.3 s to 1.5 s). Based on a related determining condition, there is no interference period in this window. Therefore, all found steps are reserved.

Step Quantity Calculation

A quantity in this window is counted based on an obtained peak point corresponding to each period, to obtain the final quantity of steps in this window. The quantity of steps in this window is 6, and the signal that is not processed will continue to be processed in a next window.

Parameters Updating

Parameters such as a state flag, a location of a peak point in each period, a corresponding feature value, and a time flag of a current window are updated.

Finally, the method for counting steps counts 97 steps. Actually, the tester walks 100 steps (one step of a wearing foot is counted as one step). The accuracy is 97.0%.

Figure 5:
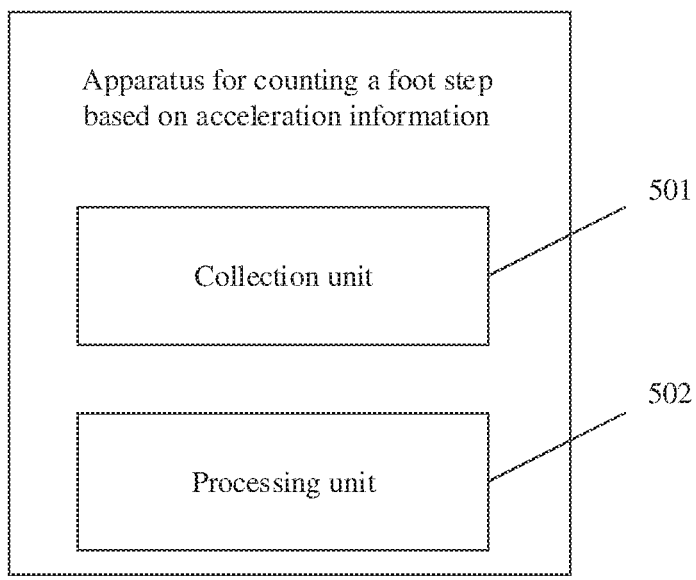
FIG. 5 is a structural diagram of an apparatus for counting foot step based on acceleration information according to this application.

FIG. 5 provides an apparatus for counting a foot step based on acceleration information. The apparatus includes a collection unit 501 and a processing unit 502.

The collection unit 501 is configured to collect an original signal in a specified time interval.

The processing unit 502 is configured to: perform combined acceleration processing on the original signal to obtain a combined acceleration signal; combine n data points of the combined acceleration signal into one data segment, extract a feature point of the data segment, and transform feature points of all data segments into a feature point signal, where the feature point is a sum of maximum fluctuation values of a front half segment and a rear half segment of each axis of the data segment; analyze the feature point signal to obtain a stable stage and a fluctuation stage of the feature point signal, and perform interference period elimination on the feature point signal with the stable stage and the fluctuation stage according to a specified motion rule to obtain a feature point signal obtained after the interference elimination; and count a quantity of wave crests of the feature point signal obtained after the interference elimination, where the quantity of wave crests is a quantity of steps.

Optionally, a value range of n is an integer within [8, 12].

Optionally, the processing unit 502 is specifically configured to: when the feature point signal is considered as a stable stage of walking by default, extract every m1 feature points of the feature point signal, determine a group of first amplitude differences between the m1 feature points and a group of first amplitude absolute-values of the m1 feature points, and if the group of first amplitude differences falls within a first specified range and the group of first amplitude absolute-values is less than a first threshold, determine the m1 feature points as the stable stage of walking; if a group of second amplitude differences between m2 feature points after the m1 feature points falls within a second specified range and a group of second amplitude absolute-values of the m2 feature points is greater than the first threshold and less than a second threshold, determine the m2 feature points as a fluctuation stage of walking; search a remaining interval of a feature point signal in a non-walking state for a stable stage of running, extract every m3 feature points in the remaining interval, determine a group of third amplitude differences between the m3 feature points and a group of third amplitude absolute-values of the m3 feature points, and if the group of amplitude absolute-values of the m3 feature points is less than a third threshold and the group of third amplitude differences falls within the first specified range, determine the m3 feature points as the stable stage of running; and extract the last m4 feature points after the m3 feature points, determine a group of fourth amplitude differences between the m4 feature points and a group of fourth amplitude absolute-values of the m4 feature points, and if the group of fourth amplitude absolute-values is greater than the third threshold and the group of fourth amplitude differences falls within the second specified range, determine the m4 feature points as a fluctuation stage of running, where values of m1, m2, m3, and m4 are all integers greater than or equal to 3.

Optionally, the processing unit 502 is specifically configured to: determine wave crest locations in the stable stage and the fluctuation stage, preliminarily determine each wave crest as a step quantity location, calculate a difference between two adjacent step quantities, sequentially form all differences into a difference list, divide the difference list into a walking state and a running state based on a corresponding step quantity location, search the difference list in the walking state for an $x^{th}$ difference and an $(x+1)^{th}$ difference that are less than a first difference threshold, and if a sum of the $x^{th}$ difference and the $(x+1)^{th}$ difference is less than a second difference threshold, remove an intermediate wave crest of the $x^{th}$ difference and the $(x+1)^{th}$ difference; and search the difference list in the running state for a $y^{th}$ difference and a $(y+1)^{th}$ difference that are less than a third difference threshold, and if a sum of the $y^{th}$ difference and the $(y+1)^{th}$ difference is less than a fourth difference threshold, remove an intermediate wave crest of the $y^{th}$ difference and the $(y+1)^{th}$ difference.

Figure 6:
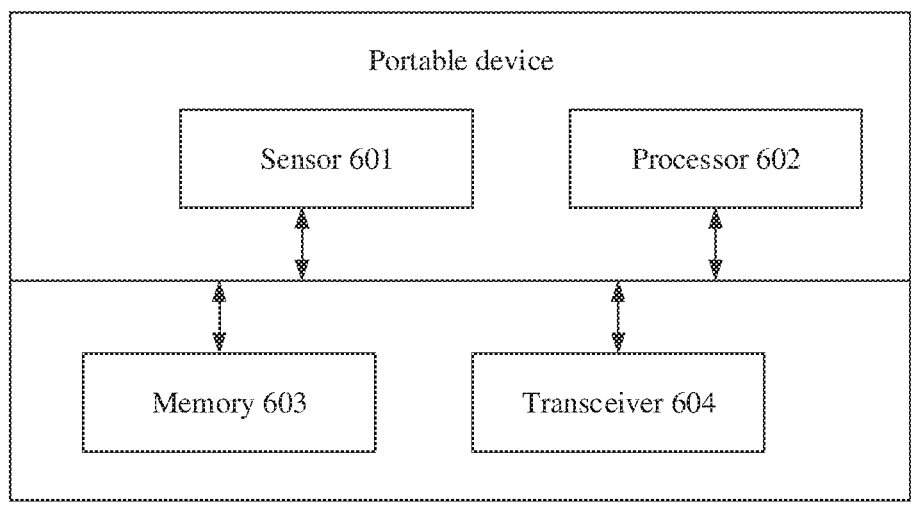
FIG. 6 is a structural diagram of a portable device according to this application.

FIG. 6 provides a portable device. The device includes a sensor 601, a processor 602, a memory 603, and a transceiver 604. The processor may be connected to the sensor, the memory, and the transceiver by using a bus. Certainly, in actual application, the processor may also be connected to the sensor, the memory, and the transceiver in another manner.

The sensor 601 is configured to collect an original signal in a specified time interval.

The processor 602 is configured to: perform combined acceleration processing on the original signal to obtain a combined acceleration signal; combine n data points of the combined acceleration signal into one data segment, extract a feature point of the data segment, and transform feature points of all data segments into a feature point signal, where the feature point is a sum of maximum fluctuation values of a front half segment and a rear half segment of each axis of the data segment; analyze the feature point signal to obtain a stable stage and a fluctuation stage of the feature point signal, and perform interference period elimination on the feature point signal with the stable stage and the fluctuation stage according to a specified motion rule to obtain a feature point signal obtained after the interference elimination; and count a quantity of wave crests of the feature point signal obtained after the interference elimination, where the quantity of wave crests is a quantity of steps.

Optionally, a value range of n is an integer within [8, 12].

Optionally, the processor 602 is specifically configured to: when the feature point signal is considered as a stable stage of walking by default, extract every m1 feature points of the feature point signal, determine a group of first amplitude differences between the m1 feature points and a group of first amplitude absolute-values of the m1 feature points, and if the group of first amplitude differences falls within a first specified range and the group of first amplitude absolute-values is less than a first threshold, determine the m1 feature points as the stable stage of walking; if a group of second amplitude differences between m2 feature points after the m1 feature points falls within a second specified range and a group of second amplitude absolute-values of the m2 feature points is greater than the first threshold and less than a second threshold, determine the m2 feature points as a fluctuation stage of walking; search a remaining interval of a feature point signal in a non-walking state for a stable stage of running, extract every m3 feature points in the remaining interval, determine a group of third amplitude differences between the m3 feature points and a group of third amplitude absolute-values of the m3 feature points, and if the group of amplitude absolute-values of the m3 feature points is less than a third threshold and the group of third amplitude differences falls within the first specified range, determine the m3 feature points as the stable stage of running; and extract the last m4 feature points after the m3 feature points, determine a group of fourth amplitude differences between the m4 feature points and a group of fourth amplitude absolute-values of the m4 feature points, and if the group of fourth amplitude absolute-values is greater than the third threshold and the group of fourth amplitude differences falls within the second specified range, determine the m4 feature points as a fluctuation stage of running, where values of m1, m2, m3, and m4 are all integers greater than or equal to 3.

Optionally, the processor 602 is specifically configured to: determine wave crest locations in the stable stage and the fluctuation stage, preliminarily determine each wave crest as a step quantity location, calculate a difference between two adjacent step quantities, sequentially form all differences into a difference list, divide the difference list into a walking state and a running state based on a corresponding step quantity location, search the difference list in the walking state for an $x^{th}$ difference and an $(x+1)^{th}$ difference that are less than a first difference threshold, and if a sum of the $x^{th}$ difference and the $(x+1)^{th}$ difference is less than a second difference threshold, remove an intermediate wave crest of the $x^{th}$ difference and the $(x+1)^{th}$ difference; and search the difference list in the running state for a $y^{th}$ difference and a $(y+1)^{th}$ difference that are less than a third difference threshold, and if a sum of the $y^{th}$ difference and the $(y+1)^{th}$ difference is less than a fourth difference threshold, remove an intermediate wave crest of the $y^{th}$ difference and the $(y+1)^{th}$ difference.

It should be noted that the processor 602 herein may be one processing element, or may be a general term for a plurality of processing elements. For example, the processing element may be a central processing unit (Central Processing Unit, CPU), may be an application specific integrated circuit (Application Specific Integrated Circuit, ASIC), or may be configured as one or more integrated circuits for implementing this embodiment of this application, for example, one or more microprocessors (digital signal processor, DSP), or one or more field programmable gate arrays (Field Programmable Gate Array, FPGA).

Another aspect of this application further provides a computer-readable storage medium. The computer-readable storage medium stores a computer program used to exchange electronic data, and the computer program enables a computer to perform the method shown in FIG. 2.

Another aspect of this application provides a computer program product. The computer program product includes a non-transitory computer-readable storage medium storing a computer program, and the computer program can be operated to enable a computer to perform the method shown in FIG. 2.

It should be noted that, for brief description, the foregoing method embodiments are represented as a series of actions. However, a person skilled in the art should appreciate that this application is not limited to the described order of the actions, because according to this application, some steps may be performed in other orders or simultaneously. In addition, it should be further appreciated by a person skilled in the art that the embodiments described in this specification all are preferred embodiments, and the involved actions and modules are not necessarily required by this application.

In the foregoing embodiments, the description of each embodiment has respective focuses. For a part that is not described in detail in an embodiment, refer to related descriptions in other embodiments.

In the several embodiments provided in this application, it should be understood that the disclosed apparatus may be implemented in other manners. For example, the described apparatus embodiments are merely examples. For example, the unit division is merely logical function division and may be other division in actual implementation. For example, a plurality of units or components may be combined or integrated into another system, or some features may be ignored or not be performed. In addition, the displayed or discussed mutual couplings or direct couplings or communication connections may be implemented through some interfaces. The indirect couplings or communication connections between the apparatuses or units may be implemented in electronic or another form.

The units described as separate parts may or may not be physically separate, and parts displayed as units may or may not be physical units, in other words, may be located in one position, or may be distributed on a plurality of network units. Some or all of the units may be selected based on actual requirements to achieve the objectives of the solutions in the embodiments.

In addition, functional units in the embodiments of this application may be integrated into one processing unit, or each of the units may exist alone physically, or two or more units may be integrated into one unit. The integrated units may be implemented in a form of hardware, or may be implemented in a form of a software functional unit.

When the integrated unit is implemented in the form of a software functional unit and sold or used as an independent product, the integrated unit may be stored in a computer-readable storage. Based on such an understanding, the technical solutions of this application essentially, or the part contributing to the prior art, or all or some of the technical solutions may be implemented in the form of a software product. The software product is stored in a storage medium and includes several instructions for instructing a computer device (which may be a personal computer, a server, or a network device) to perform all or some of the steps of the methods described in the embodiments of this application. The foregoing memory includes: any medium that can store program code, such as a USB flash drive, a read-only memory (ROM, Read-Only Memory), a random access memory (RAM, Random Access Memory), a removable hard disk, a magnetic disk, or an optical disc.

What is disclosed above is merely example embodiments of this application, and certainly is not intended to limit the protection scope of this application. A person of ordinary skill in the art may understand that all or some of processes that implement the foregoing embodiments and equivalent modifications made in accordance with the claims of this application shall fall within the scope of this application.

What is claimed is:

1. A method for counting a foot step based on acceleration information, wherein the method comprises:
   collecting an original signal in a specified time interval;
   performing combined acceleration processing on the original signal to obtain a combined acceleration signal;
   combining n data points of the combined acceleration signal into a data segment;
   extracting a feature point of the data segment, wherein the feature point is a sum of maximum fluctuation values of a front half segment and a rear half segment of each axis of the data segment;
   transforming feature points of all data segments into a feature point signal;
   analyzing the feature point signal to obtain a stable stage and a fluctuation stage of the feature point signal;
   performing interference period elimination on the feature point signal with the stable stage and the fluctuation stage according to a specified motion rule to obtain a second feature point signal; and
   counting a quantity of wave crests of the second feature point signal, wherein the quantity of wave crests is a quantity of steps.

2. The method of claim 1, wherein a value range of n is an integer within a closed interval of [8, 12].

3. The method of claim 1, further comprising:
   setting the feature point signal as a stable stage of walking;
   extracting m1 feature points of the feature point signal, wherein a value of m1 is an integer greater than or equal to 3;
   determining a group of first amplitude differences between the m1 feature points and a group of first amplitude absolute values of the m1 feature points;
   setting the m1 feature points as the stable stage of walking when the group of first amplitude differences falls within a first specified range and the group of first amplitude absolute values is less than a first threshold;
   setting m2 feature points after the m1 feature points as a fluctuation stage of walking when a group of second amplitude differences between the m2 feature points falls within a second specified range and a group of second amplitude absolute values of the m2 feature points is greater than the first threshold and less than a second threshold, wherein a value of m2 is an integer greater than or equal to 3;
   searching a remaining interval of the feature point signal in a non-walking state for a stable stage of running;
   extracting m3 feature points in the remaining interval, wherein a value of m3 is an integer greater than or equal to 3;
   determining a group of third amplitude differences between the m3 feature points and a group of third amplitude absolute values of the m3 feature points;
   setting the m3 feature points as the stable stage of running when the group of third amplitude absolute values is less than a third threshold and the group of third amplitude differences falls within the first specified range;
   extracting m4 feature points after the m3 feature points, wherein a value of m4 is an integer greater than or equal to 3;
   determining a group of fourth amplitude differences between the m4 feature points and a group of fourth amplitude absolute values of the m4 feature points; and
   setting the m4 feature points as a fluctuation stage of running when the group of fourth amplitude absolute values is greater than the third threshold and the group of fourth amplitude differences falls within the second specified range.

4. The method of claim 3, further comprising:
   determining wave crest locations in the stable stage and the fluctuation stage;
   preliminarily setting each wave crest as a step quantity location;
   calculating a difference between two adjacent step quantities;
   sequentially forming all differences into a difference list;
   dividing the difference list into a walking state and a running state based on a corresponding step quantity location;
   searching the difference list in the walking state for an $x^{th}$ difference and an $(x+1)^{th}$ difference that are less than a first difference threshold;
   removing an intermediate wave crest of the $x^{th}$ difference and the $(x+1)^{th}$ difference when a sum of the $x^{th}$ difference and the $(x+1)^{th}$ difference is less than a second difference threshold;
   searching the difference list in the running state for a $y^{th}$ difference and a $(y+1)^{th}$ difference that are less than a third difference threshold; and
   removing an intermediate wave crest of the $y^{th}$ difference and the $(y+1)^{th}$ difference when a sum of the $y^{th}$ difference and the $(y+1)^{th}$ difference is less than a fourth difference threshold.

5. A portable device, comprising:
   a sensor configured to collect an original signal in a specified time interval; and
   a processor coupled to the sensor and configured to:
      perform combined acceleration processing on the original signal to obtain a combined acceleration signal;
      combine n data points of the combined acceleration signal into a data segment;
      extract a feature point of the data segment, wherein the feature point is a sum of maximum fluctuation values of a front half segment and a rear half segment of each axis of the data segment;
      transform feature points of all data segments into a feature point signal;
      analyze the feature point signal to obtain a stable stage and a fluctuation stage of the feature point signal;
      perform interference period elimination on the feature point signal with the stable stage and the fluctuation stage according to a specified motion rule to obtain a second feature point signal; and
      count a quantity of wave crests of the second feature point signal, wherein the quantity of wave crests is a quantity of steps.

6. The portable device of claim 5, wherein a value range of n is an integer within a closed interval of [8, 12].

7. The portable device of claim 5, wherein the processor is further configured to:
set the feature point signal as a stable stage of walking;
extract m1 feature points of the feature point signal, wherein a value of m1 is an integer greater than or equal to 3;
determine a group of first amplitude differences between the m1 feature points and a group of first amplitude absolute values of the m1 feature points;
set the m1 feature points as the stable stage of walking when the group of first amplitude differences falls within a first specified range and the group of first amplitude absolute values is less than a first threshold;
determine m2 feature points after the m1 feature points as a fluctuation stage of walking when a group of second amplitude differences between the m2 feature points falls within a second specified range and a group of second amplitude absolute values of the m2 feature points is greater than the first threshold and less than a second threshold, wherein a value of m2 is an integer greater than or equal to 3;
search a remaining interval of the feature point signal in a non-walking state for a stable stage of running;
extract m3 feature points in the remaining interval, wherein a value of m3 is an integer greater than or equal to 3;
determine a group of third amplitude differences between the m3 feature points and a group of third amplitude absolute values of the m3 feature points;
set the m3 feature points as the stable stage of running when the group of third amplitude absolute values is less than a third threshold and the group of third amplitude differences falls within the first specified range;
extract m4 feature points after the m3 feature points, wherein a value of m4 is an integer greater than or equal to 3;
determine a group of fourth amplitude differences between the m4 feature points and a group of fourth amplitude absolute values of the m4 feature points; and
set the m4 feature points as a fluctuation stage of running when the group of fourth amplitude absolute values is greater than the third threshold and the group of fourth amplitude differences falls within the second specified range.

8. The portable device of claim 7, wherein the processor is further configured to:
determine wave crest locations in the stable stage and the fluctuation stage;
determine preliminarily set each wave crest as a step quantity location;
calculate a difference between two adjacent step quantities;
sequentially form all differences into a difference list;
divide the difference list into a walking state and a running state based on a corresponding step quantity location;
search the difference list in the walking state for an $x^{th}$ difference and an $(x+1)^{th}$ difference that are less than a first difference threshold;
remove an intermediate wave crest of the $x^{th}$ difference and the $(x+1)^{th}$ difference when a sum of the $x^{th}$ difference and the $(x+1)^{th}$ difference is less than a second difference threshold;
search the difference list in the running state for a $y^{th}$ difference and a $(y+1)^{th}$ difference that are less than a third difference threshold; and
remove an intermediate wave crest of the $y^{th}$ difference and the $(y+1)^{th}$ difference when a sum of the $y^{th}$ difference and the $(y+1)^{th}$ difference is less than a fourth difference threshold.

9. A computer program product comprising computer-executable instructions for storage on a non-transitory computer-readable medium that, when executed by a processor, cause a portable device to:
collect an original signal in a specified time interval;
perform combined acceleration processing on the original signal to obtain a combined acceleration signal;
combine n data points of the combined acceleration signal into a data segment;
extract a feature point of the data segment, wherein the feature point is a sum of maximum fluctuation values of a front half segment and a rear half segment of each axis of the data segment;
transform feature points of all data segments into a feature point signal;
analyze the feature point signal to obtain a stable stage and a fluctuation stage of the feature point signal;
perform interference period elimination on the feature point signal with the stable stage and the fluctuation stage according to a specified motion rule to obtain a second feature point signal; and
count a quantity of wave crests of the second feature point signal, wherein the quantity of wave crests is a quantity of steps.

10. The computer program product of claim 9, wherein a value range of n is an integer within a closed interval of [8, 12].

11. The computer program product of claim 9, wherein the computer-executable instructions further cause the portable device to:
set the feature point signal as a stable stage of walking;
extract m1 feature points of the feature point signal, wherein a value of m1 is an integer greater than or equal to 3;
determine a group of first amplitude differences between the m1 feature points and a group of first amplitude absolute values of the m1 feature points;
set the m1 feature points as the stable stage of walking when the group of first amplitude differences falls within a first specified range and the group of first amplitude absolute values is less than a first threshold;
set m2 feature points after the m1 feature points as a fluctuation stage of walking when a group of second amplitude differences between the m2 feature points falls within a second specified range and a group of second amplitude absolute values of the m2 feature points is greater than the first threshold and less than a second threshold, wherein a value of m2 is an integer greater than or equal to 3;
search a remaining interval of the feature point signal in a non-walking state for a stable stage of running;
extract m3 feature points in the remaining interval, wherein a value of m3 is an integer greater than or equal to 3;
determine a group of third amplitude differences between the m3 feature points and a group of third amplitude absolute values of the m3 feature points;
set the m3 feature points as the stable stage of running when the group of third amplitude absolute values is less than a third threshold and the group of third amplitude differences falls within the first specified range;

extract m4 feature points after the m3 feature points, wherein a value of m4 is an integer greater than or equal to 3;

determine a group of fourth amplitude differences between the m4 feature points and a group of fourth amplitude absolute values of the m4 feature points; and set the m4 feature points as a fluctuation stage of running when the group of fourth amplitude absolute values is greater than the third threshold and the group of fourth amplitude differences falls within the second specified range.

12. The computer program product of claim 11, wherein the computer-executable instructions further cause the portable device to:

determine wave crest locations in the stable stage and the fluctuation stage;

preliminarily set each wave crest as a step quantity location;

calculate a difference between two adjacent step quantities;

sequentially form all differences into a difference list;

divide the difference list into a walking state and a running state based on a corresponding step quantity location;

search the difference list in the walking state for an $x^{th}$ difference and an $(x+1)^{th}$ difference that are less than a first difference threshold;

remove an intermediate wave crest of the $x^{th}$ difference and the $(x+1)^{th}$ difference when a sum of the $x^{th}$ difference and the $(x+1)^{th}$ difference is less than a second difference threshold;

search the difference list in the running state for a $y^{th}$ difference and a $(y+1)^{th}$ difference that are less than a third difference threshold; and remove an intermediate wave crest of the $y^{th}$ difference and the $(y+1)^{th}$ difference when a sum of the $y^{th}$ difference and the $(y+1)^{th}$ difference is less than a fourth difference threshold.

13. The computer program product of claim 9, wherein the computer-executable instructions further cause the portable device to update a state flag of the specified time interval.

14. The computer program product of claim 9, wherein the computer-executable instructions further cause the portable device to update a time flag.

15. The computer program product of claim 9, wherein the computer-executable instructions further cause the portable device to update a location of a peak point in each period.

16. The computer program product of claim 9, wherein the computer-executable instructions further cause the portable device to update a corresponding feature value.

17. The portable device of claim 5, wherein the processor is further configured to update a state flag of the specified time interval.

18. The portable device of claim 5, wherein the processor is further configured to update a time flag.

19. The portable device of claim 5, wherein the processor is further configured to update a location of a peak point in each period.

20. The portable device of claim 5, wherein the processor is further configured to update a corresponding feature value.

* * * * *

UNITED STATES PATENT AND TRADEMARK OFFICE
CERTIFICATE OF CORRECTION

PATENT NO. : 11,426,627 B2
APPLICATION NO. : 16/640850
DATED : August 30, 2022
INVENTOR(S) : Yixin Chen et al.

It is certified that error appears in the above-identified patent and that said Letters Patent is hereby corrected as shown below:

In the Claims

Claim 8, Column 15, Line 54: "determine preliminary set" should read "preliminary set"

Signed and Sealed this
Twenty-fifth Day of October, 2022

Katherine Kelly Vidal
*Director of the United States Patent and Trademark Office*